(12) United States Patent
Chen et al.

(10) Patent No.: US 8,913,718 B2
(45) Date of Patent: Dec. 16, 2014

(54) METHOD FOR IDENTIFYING NANO TEXTILE

(76) Inventors: Jun Chen, Suzhou (CN); Yanguang Lu, Suzhou (CN); Liuyan Yang, Suzhou (CN); Juanhong Gu, Suzhou (CN); Tianyu Yang, Suzhou (CN); Yuqiong Tang, Suzhou (CN)

( * ) Notice: Subject to any disclaimer, the term of this patent is extended or adjusted under 35 U.S.C. 154(b) by 315 days.

(21) Appl. No.: 13/459,073

(22) Filed: Apr. 27, 2012

(65) Prior Publication Data
US 2012/0213335 A1 Aug. 23, 2012

Related U.S. Application Data

(63) Continuation-in-part of application No. PCT/CN2009/074650, filed on Oct. 28, 2009.

(51) Int. Cl.
*G01N 23/20* (2006.01)
*H01J 37/26* (2006.01)
*G01N 33/36* (2006.01)

(52) U.S. Cl.
CPC .................. *G01N 33/367* (2013.01)
USPC ............................................. 378/71; 250/307

(58) Field of Classification Search
CPC ................................................ G01N 33/367
USPC ............................................. 378/71; 250/307
See application file for complete search history.

(56) References Cited

U.S. PATENT DOCUMENTS

2009/0186276 A1 * 7/2009 Zhamu et al. ................ 429/221
2009/0305135 A1 * 12/2009 Shi et al. ...................... 429/217

* cited by examiner

*Primary Examiner* — Hoon Song
*Assistant Examiner* — Danielle Fox
(74) *Attorney, Agent, or Firm* — Matthias Scholl P.C.; Matthias Scholl

(57) ABSTRACT

A method for identifying a nano textile, including: (1) determining whether a textile belongs to a woven fabric or a non-woven fabric by appearance; and (2) when the textile is a woven fabric, determining whether the woven fabric is a nano textile according to the surface grains of the woven fabric and a finishing material for the woven fabric; or when the textile is a non-woven fabric, determining whether the non-woven fabric is a nano textile according to the fiber diameter and a fused material of the non-woven fabric.

5 Claims, 9 Drawing Sheets a b c d

METHOD FOR IDENTIFYING NANO TEXTILE

CROSS-REFERENCE TO RELATED APPLICATIONS

This application is a continuation-in-part of International Patent Application No. PCT/CN2009/074650 with an international filing date of Oct. 28, 2009, designating the United States, now pending. The contents of all of the aforementioned applications, including any intervening amendments thereto, are incorporated herein by reference.

CORRESPONDENCE ADDRESS

Inquiries from the public to applicants or assignees concerning this document should be directed to: MATTHIAS SCHOLL P.C., ATTN.: DR. MATTHIAS SCHOLL ESQ., 14781 MEMORIAL DRIVE, SUITE 1319, HOUSTON, Tex. 77079.

BACKGROUND OF THE INVENTION

1. Field of the Invention

The invention relates to the technical field of textile identification, and more particularly to a method for identifying a nano textile.

2. Description of the Related Art

As an emerging technology, nanotechnology has attracted more and more attention. At present, the usability of nanotechnology in the textile field is increasingly high, and various functional fabrics with nanostructure units have been developed and produced, such as waterproof fabrics, oilproof fabrics, soil release fabrics, antibacterial fabrics, anti-ultraviolet fabrics, etc.

According to the regulations from ISO TS 27687-2008 "Terminology for Nanomaterials", at least one dimension of a material structure in three-dimensional space is in nano scale (geometric dimension in the range of 1-100 nm), or only the materials composed of nanostructure units and provided with special characteristics can be used as nanomaterials. The characteristic of nanomaterials lies in the large specific surface area, which increases the surface energy and activity of nanomaterials. Thus, the small-size effect, surface or interface effect, quantum size effect, and macroscopic quantum tunneling effect are generated, and the specificity can be observed from its chemical and physical (such as heat, light, and electromagnet) properties. There is no authoritative definition and explanation for a nano textile at present, and the identification about a nano textile is in the absence of uniform standards.

In view of the demands and limitations of practical production, the nano textiles are defined as textiles made of nanomaterials or processed by nanotechnology and provided with unique functions. The microstructure of fiber of the textile meets the requirements of nano scale or has the functional characteristics of strange surface and interface through the contact and fusion with dissimilar materials in nano scale. The cotton and silk woven fabric is manufactured into textiles with specific functions mainly through arranging the nano powder materials on the fabric surface, the criterion for determining the nano textile is to detect whether the material on the nano textile is a nano-scale material (the three-dimensional sizes are all in nano scale, that is, the average grain size is smaller than 100 nm); the unwoven fabric is manufactured into nanofibers mainly through electrostatic spinning, the nanomaterials can also be fused in fiber to be manufactured into composite nanofibers, and the criterion for determining the nano textile is to detect the average size and unit structure (for example, the two-dimensional sizes are all in nano scale, and the diameter of some fibers is smaller than 100 nm) of fiber and whether the diameter distribution is uniform. In the detection of unwoven fabric, such regulation "the diameter of some fibers is smaller than 100 nm" takes into account that all fibers are not nano-scale fibers in the prior art. Furthermore, the nano-characters of the fused nanomaterials are not required to be detected, because when the fibers are nanofibers, and the nanomaterials can be detected, whether the material is in nano scale can be judged.

The functional properties of the novel nano textile provides more conveniences for people's life, thus the global demand for nano textiles is increasing, and the market share of nano textiles is also gradually expanding. However, after the textiles are modified by using nanotechnology or finished with nanomaterials, what the reaction of nano textiles on the micro-interface will be, will the ecological effect happen, and whether biological effects and a certain toxicant mechanism are produced to human body, concrete studies will be required for solving these problems after the detection and classification of nano textiles. The establishment of the identification method for nano textiles is the basis of a series of studies on nano textiles.

SUMMARY OF THE INVENTION

In view of the above-described problems, it is one objective of the invention to provide a method for identifying and detecting a nano textile. The method can be suitable for textiles in any form such as woven fabric, knitted fabric, coated fabric, laminated fabric, and non-woven fabric.

To achieve the above objective, in accordance with one embodiment of the invention, there is provided a method for identifying a nano textile, comprising:

(1) determining whether a textile belongs to a woven fabric or a non-woven fabric by appearance; and
(2) when the textile is a woven fabric, determining whether the woven fabric is a nano textile according to the surface grains of the woven fabric and a finishing material for the woven fabric; or when the textile is a non-woven fabric, determining whether the non-woven fabric is a nano textile according to the fiber diameter and a fused material of the non-woven fabric.

In a class of this embodiment, in step (2), a method for determining whether the woven fabric is a nano textile comprises:

A. detecting the woven fabric using a scanning electron microscopy, and setting a plurality of observation areas or observation points for elemental analysis according to grains on the surface of the woven fabric; and
B. ascertaining whether the determination of the crystal form and grain size of the finishing material in the grains is required according to the result of elemental analysis in step A.

This is because the finishing material (i.e., nanomaterial) provided with nano-scale grains comprising Ti, Zn, or Ag elements is formed through agglomeration and accumulation, and its grain size does not reflect the real grain size of the finishing material.

In step B, if the grains in the elemental analysis result do not comprise Ti, Zn, or Ag element, the identification procedure ends, and the textile is not a nano textile; if the grains in the elemental analysis result comprise Ti, Zn, or Ag element, the crystal form and grain size of the finishing material in the grains on the woven fabric is detected by X-ray diffraction;

whether the textile is a nano textile is judged according to whether the average grain size of the finishing material is smaller than 100 nm.

In a class of this embodiment, the X-ray diffraction detection method comprises: scanning the textile on an X-ray diffractometer; taking a two times diffraction angle as a horizontal coordinate and a diffracted intensity as a vertical coordinate; determining the crystal form of the finishing material in the grains on the textile according to the relationship between the characteristic peak position and intensity; and calculating the average grain size of the finishing material in the grains according to the Scherrer formula.

In the method, when the average grain size of the finishing material is smaller than 100 nm, the textile is a nano textile, and the identification procedure ends; when the average grain size of the finishing material is equal to or greater than 100 nm, the textile is not a nano textile.

In a class of this embodiment, in step (2), a method for determining whether the non-woven fabric is a nano textile comprises:
  a. detecting the non-woven fabric using a scanning electron microscopy, and determining whether the non-woven fabric is a nano textile according to the diameter of fibers; and
  b. determining whether the elemental analysis of fibers is carried out according to the result in step a.

In the method, when the diameter of fibers is smaller than 100 nm, the observation points of fibers are established for elemental analysis of the fibers; whether the non-woven fabric is a nano textile fused with a finishing material is judged according to the result of elemental analysis of the fibers.

In the method, when Ti, Zn, or Ag element is contained in the result of elemental analysis of the fibers, the non-woven fabric is a nano textile fused with a finishing material; otherwise, the non-woven fabric is a nano textile without being fused with a finishing material.

In a class of this embodiment, the scanning electron microscopy detection method in the method comprises: sputtering a metal conductive film on the textile surface with an ion sputter; and feeding samples into a scanning electron microscope for scanning electron microscopy imaging.

In step (1) of the method, the step of determining by appearance comprises determining whether the textile is a woven fabric or non-woven fabric according to the texture of the textile, whether the textile has obvious horizontal and longitudinal grains as well as whether the textile can be split or twisted to obtain single yarns.

The woven fabric is a woven fabric textile woven with yarns or filaments by the traditional weaving process (weaving and knitting). The non-woven fabric is flakes, fiber webs or batts (GB/T 5709-1997) manufactured by mutually combining the directional or randomly arranged fibers through friction, gripping, or sticking or in a combined way of friction, gripping, and sticking. The woven fabric and non-woven fabric can be distinguished by appearance observation: most woven fabrics have relatively coarser texture and obvious horizontal and longitudinal grains, and can be split or twisted to obtain single yarns; the non-woven fabrics have fine texture without grains, have ductility during the tearing process, and cannot be split or twisted to obtain single yarns. Therefore, whether a textile is a woven fabric can be determined by appearance observation; if a textile is provided with coarser texture and obvious horizontal and longitudinal grains, and can be split or twisted to obtain single yarns, the textile is a woven fabric; if a textile is thin and light, fine in texture, free from grain, has adsorbability and ductility during the tearing process, and cannot be split or twisted to obtain single yarns, the textile is a non-woven fabric.

Specifically, the method comprises:
determining whether the textile is a woven fabric, if the textile is a woven fabric, executing the identification step of a nano woven fabric, otherwise, executing the identification step of a nano non-woven fabric;

detecting the woven fabric using a scanning electron microscopy, observing whether there are grains on the surface of the woven fabric, and performing elemental analysis to more than four observation points using the scanning electron microscope; if there are grains on the surface of the woven fabric after observation with the scanning electron microscope, the observation points in elemental analysis are grains of 4 areas. If there is no grain on the surface of the woven fabric, four observation points in elemental analysis are taken randomly. Whether Ti, Zn, or Ag element is contained in the result of elemental analysis is judged, and if the Ti, Zn, or Ag element is contained, the woven fabric is detected by X-ray diffraction, so as to determine the crystal form and average grain size of the material finished on the surface of the woven fabric and comprising Ti, Zn, or Ag element; otherwise, the detection procedure ends when the woven fabric is determined as a non-nano textile; determining whether the average grain size of the nanomaterial used for textile finishing is smaller than 100 nm, if the average grain size is smaller than 100 nm, the detection procedure ends when the woven fabric is determined as a nano textile, otherwise, the detection procedure ends when the woven fabric is determined as a non-nano textile.

The identification step of a non-woven fabric comprises: detecting a non-woven fabric using a scanning electron microscopy, measuring the fiber diameter, and performing elemental analysis to more than four observation points using the scanning electron microscope; whether there is fiber with diameter smaller than 100 nm in the fiber diameter measuring result, and if there are fibers with diameter smaller than 100 nm, the non-woven fabric is determined as a nano textile, and whether the Ti, Zn, or Ag element is contained is judged according to the result of elemental analysis, otherwise, the detection procedure ends when the non-woven fabric is not determined as a nano textile. In the step, if there are grains on the surface of the woven fabric through observation with the scanning electron microscope, the observation points in elemental analysis are grains.

Specifically, the scanning electron microscopy detection method comprises two steps of sample preparation and sample detection.

The sample preparation step can be executed according to the following procedures: randomly shearing five 5 mm×5 mm samples on a textile with a pair of clean scissors during the sampling process, and then marking the to-be-detected surfaces; holding the samples with a pair of forceps and fixing the samples on a sample support stuck with conductive adhesive tapes, and keeping the to-be-detected surfaces of the samples upward; moving the sample support carried with samples to an ion sputter (HITACHI E-1010), and then sputtering a metal conductive film on the sample support.

The sample detection is carried out as follows: transferring the sample support sputtered with the metal conductive film in a scanning electron microscope sample room, and vacuumizing until the scanning electron microscopy test can be carried out; when the scanning electron microscopy test is carried out, randomly selecting four areas for each sample for observation, and magnifying to be favorable for observing the nano structure.

The specific parameters are adjusted according to the observed magnifications and definition requirements.

If there are grains on the surface of the woven fabric through observation with the scanning electron microscope, the observation points in elemental analysis are grains of four areas. If there is no grain on the surface of the woven fabric, four observation points in elemental analysis are randomly taken.

Specifically, the X-ray diffraction detection method is as follows: randomly shearing five 1 cm×1 cm samples on a textile with a pair of clean scissors, and marking the to-be-detected surfaces; holding the samples with a pair of forceps and putting the samples on a glass slide, and then flattening the samples; transferring the glass slide to a sample support for scanning; according to the obtained data, making a drawing by taking the two times diffraction angle as a horizontal coordinate and the diffracted intensity as a vertical coordinate; determining the crystal form of the finishing material according to the relationship between the characteristic peak position and intensity, and calculating the average grain size of the finishing material according to the Scherrer formula.

Some terms used in the identification method for a nano textile are summarized as follows:

Scanning electronic microscopy (SEM): the surface morphology of samples is observed mainly by using the secondary electronic signal imaging, that is, the samples are scanned using an extremely narrow electron beam, and various effects (mainly including secondary electron emission of samples) are generated under the interaction of the electron beam and samples. The topography images (sample surface magnification) generated by emitting secondary electron are collected. The detecting instrument in the prior art comprises an S-3400N scanning electron microscope from Japanese Hitachi company.

X-ray powder diffraction: X-rays are electromagnetic waves with short wavelength, the atoms in the crystal are periodically and regularly arranged, the arranged spatial period is in the same order of magnitude with the wavelength of X-rays, and X-rays produce diffraction while passing through the crystal, so that the crystal structure, texture and stress of matter can be accurately measured, and the phase analysis, qualitative analysis and quantitative analysis can be accurately carried out. The detecting instrument in the prior art comprises a D/Max-RA from Japanese Rigaku Corporation.

The detection object suitable for the identification method for a nano textile comprises natural fiber fabrics (such as cotton and silk); synthetic fiber fabrics (such as polyamide and polyester), i.e., non-woven fabric manufactured by electrostatic spinning; the nano finishing materials such as nano-zinc oxide, nano-TiO2 and nano-silver are comprised or excluded in the detection object.

Advantages of the invention are summarized below:

The invention provides a method for systematic identification of a nano structure unit on the surface of a nano textile, and the method lays a preliminary technical base for a detection system for a nano textile, and can be suitable for textiles in any form such as woven fabric, knitted fabrics, coated fabrics, laminated fabrics and non-woven fabric (made of nanomaterials or processed by nanotechnology) in the production and processing process; the method is favorable for the establishment and perfection of basic performance indexes of a nano textile, and standardizes the performance and quality testing and evaluation as well as the quality inspection, analysis and identification of textile materials using nanotechnology; the method facilitates the further perfection of product technical standards of a nano textile, and provides corresponding technical support for the implementation of security evaluation and risk management of a nano textile.

DETAILED DESCRIPTION OF THE EMBODIMENTS

Example 1

Observing an unknown textile by appearance, and determining the textile provided with coarser texture and obvious horizontal and longitudinal grains and capable of being split or twisted to obtain single yarns as a woven fabric.

Figure 1:
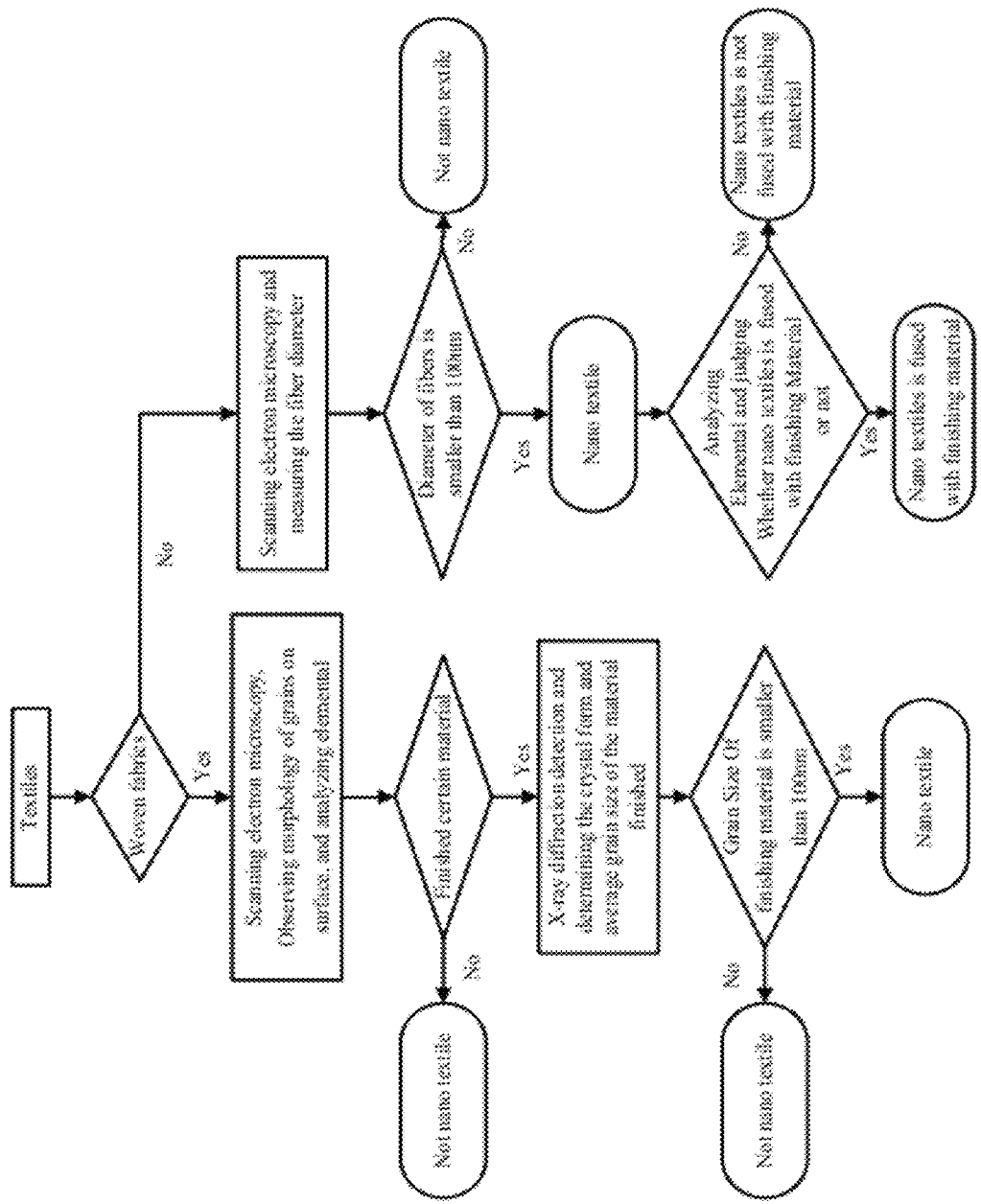
FIG. 1 is a flowchart of a method for identifying a nano textile in accordance with one embodiment of the invention.
Figure 2:
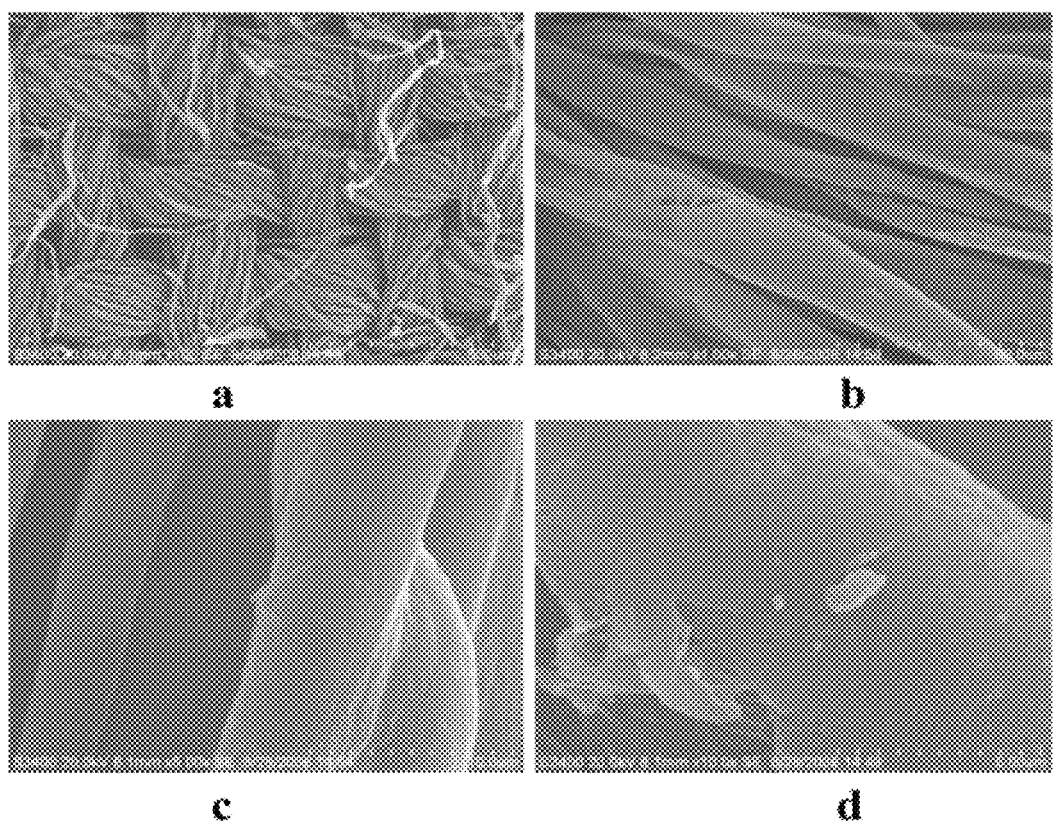
FIG. 2 shows scanning electron microscope photos of cotton fabrics in accordance with one embodiment of the invention under different multiples; wherein a, b, c, and d represent under 100 multiples, under 1,000 multiples, under 5,000 multiples, and under 10,000 multiples, respectively.
Figure 3:
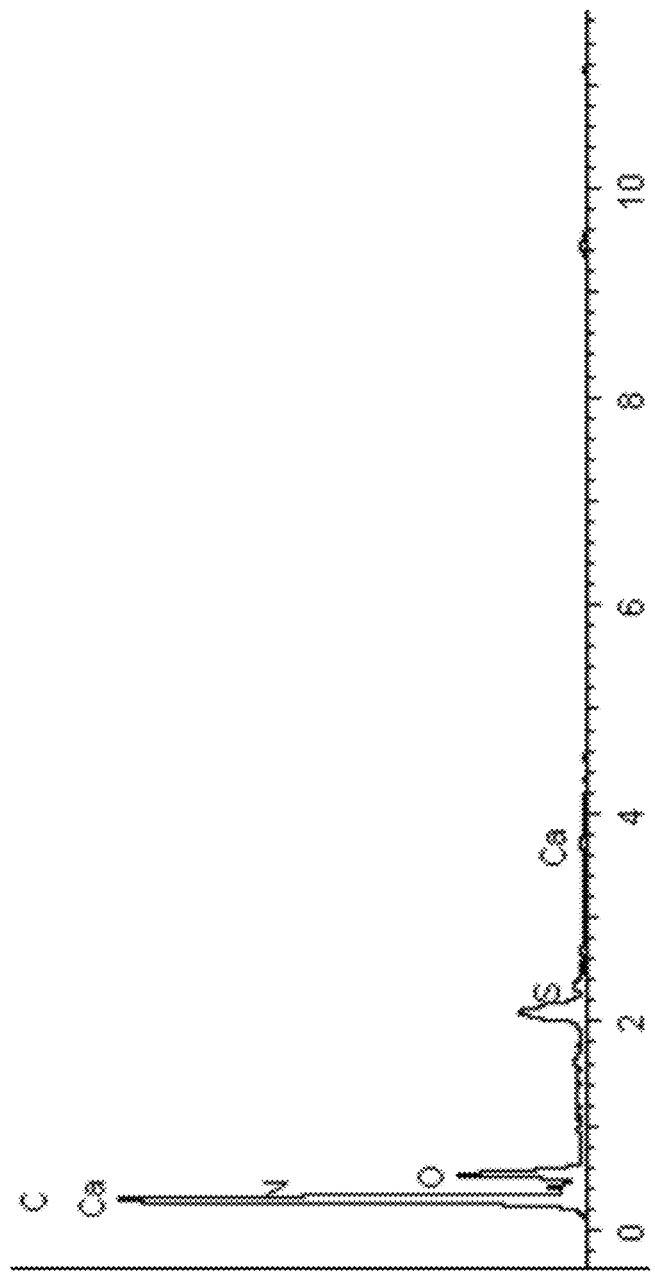
FIG. 3 is an elemental analysis (SEM) diagram in accordance with one embodiment of the invention.

Detecting the unknown textile by scanning electron microscopy: taking a cylindrical metal sample support, shearing 1 cm×1 cm unknown textile, and fixing the unknown textile on the sample support; sputtering a metal conductive film by using an ion sputter (HITACHI E-1010); transferring the sample support sputtered with the metal conductive film in an scanning electron microscope sample room, and vacuumizing until the scanning electron microscopy test can be carried out. Observing the imaging, see FIG. 2. Under a low-magnification scanning electron microscope, it is shown that the cotton threads are crisscrossed in an orderly manner, and there is no grain on the surface; under a high-magnification scanning electron microscope, it is shown that the diameter of single yarns is not uniform. Because there is no grain on the surface, four areas on the woven fabric is randomly selected for elemental analysis, see FIG. 3.

There is no Ti, Zn, or Ag element contained in the elemental analysis diagram, the major element comprises C, O, and N from cellulose, and other low-content elements are S, Ca, etc.

The textile is not determined as a nano textile according to the detection procedure above.

Example 2

Observing an unknown textile by appearance, and determining the textile provided with coarser texture and obvious horizontal and longitudinal grains and capable of being split or twisted to obtain single yarns as a woven fabric.

Detecting the unknown textile by scanning electron microscopy: randomly shearing five 5 mm×5 mm samples on the textile with a pair of clean scissors during the sampling process, and marking the to-be-detected surfaces; holding the samples with a pair of forceps and fixing the samples on a sample support stuck with conductive adhesive tapes, and keeping the to-be-detected surfaces of the samples upward; moving the sample support carried with samples to an ion sputter, and sputtering a metal conductive film on the sample support; transferring the sample support sputtered with the metal conductive film in a scanning electron microscope sample room, and vacuumizing until the scanning electron microscopy test can be carried out.

Four areas are randomly selected for observing imaging, and it's observed that there is no obvious grain on the surface of the textile. A grain is selected from each observation area for elemental analysis to obtain an elemental analysis diagram. From the elemental analysis, it is discovered that besides a large number of C, O and N elements, a certain amount of Zn element is contained, thus it indicates that the woven fabric comprises nanomaterial.

Detecting the woven fabric by X-ray diffraction: randomly shearing five 1 cm×1 cm samples on the textile with a pair of clean scissors, and marking the to-be-detected surfaces; holding the samples with a pair of forceps and putting the samples on a glass slide, and then flattening the samples; transferring the glass slide to a sample support for scanning; according to the obtained data, making a drawing by taking the two times diffraction angle as a horizontal coordinate and the diffracted intensity as a vertical coordinate; determining the crystal form of the finishing material on the woven fabric according to the relationship between the characteristic peak position and intensity, and calculating the average grain size of the finishing material according to the Scherrer formula.

The result shows that the average grain size is 270 nm, thus the textile is not determined as a nano woven fabric.

Example 3

Observing an unknown textile by appearance, and determining the textile provided with coarser texture and obvious horizontal and longitudinal grains and capable of being split or twisted to obtain single yarns as a woven fabric.

Detecting the unknown textile by scanning electron microscopy: randomly shearing five 5 mm×5 mm samples on the textile with a pair of clean scissors during the sampling process, and marking the to-be-detected surfaces; holding the samples with a pair of forceps and fixing the samples on a sample support stuck with conductive adhesive tapes, and keeping the to-be-detected surfaces of the samples upward; moving the sample support carried with samples to an ion sputter, and sputtering a metal conductive film on the sample support; transferring the sample support sputtered with the metal conductive film in a scanning electron microscope sample room, and vacuumizing until the scanning electron microscopy test can be carried out.

Figure 4:
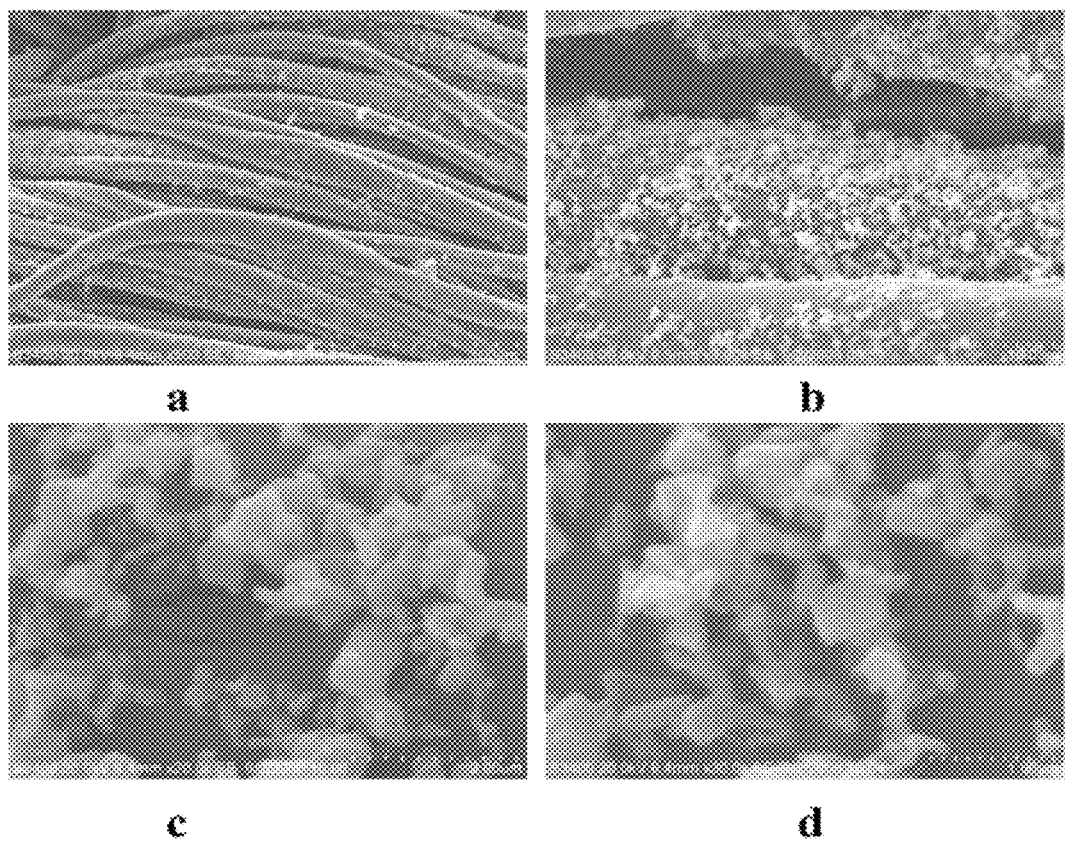
FIG. 4 shows scanning electron microscope photos of a textile in accordance with one embodiment of the invention under different multiples; wherein a, b, c, and d represent under 500 multiples, under 3,000 multiples, under 20,000 multiples, and under 30,000 multiples, respectively, and ZnO is contained.
Figure 5:
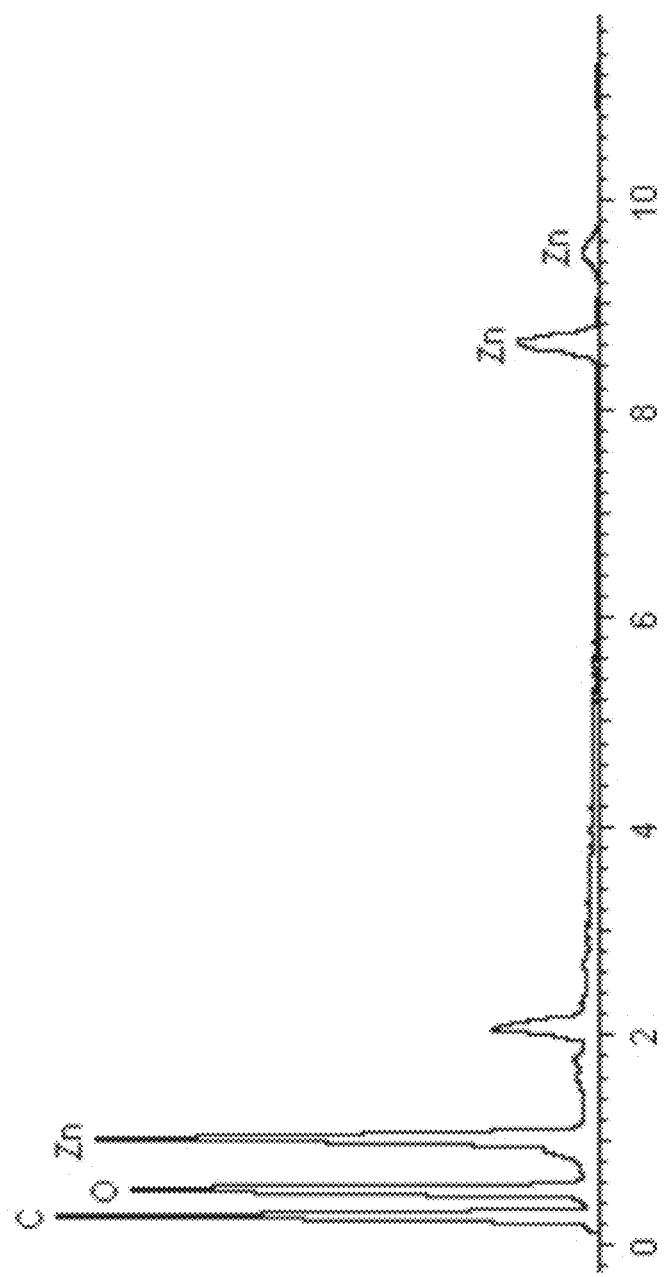
FIG. 5 is an elemental analysis (SEM) diagram in accordance with another embodiment of the invention.

Four rears are randomly selected for observing imaging, and it's observed that there are obvious grains on the surface of the textile, see FIG. 4. FIG. 4 shows that the obvious grains on the textile can be seen under 500 multiples; the grains are irregular in shape and distributed in a dispersed manner; small grains are accumulated or agglomerated to lead to wide distribution of grain size grade from grade nm to grade um, and the highest grade reaches several dozens um. A grain is selected from each observation area for elemental analysis to obtain an elemental analysis diagram. The same elemental analysis is contained in the four diagrams, and a typical diagram is selected, see FIG. 5. The elemental analysis shows that the grain has high content of Zn and O, thus it indicates that the observed grains are ZnO.

Detecting the textile by X-ray diffraction: randomly shearing five 1 cm×1 cm samples on the textile with a pair of clean scissors, and marking the to-be-detected surfaces; holding the samples with a pair of forceps and putting the samples on a glass slide, and then flattening the samples; transferring the glass slide to a sample support for scanning; according to the obtained data, making a drawing by taking the two times diffraction angle as a horizontal coordinate and the diffracted intensity as a vertical coordinate; determining the crystal form of the finishing material on the textile according to the relationship between the characteristic peak position and intensity, and calculating the average grain size of the finishing material according to the Scherrer formula.

Figure 6:
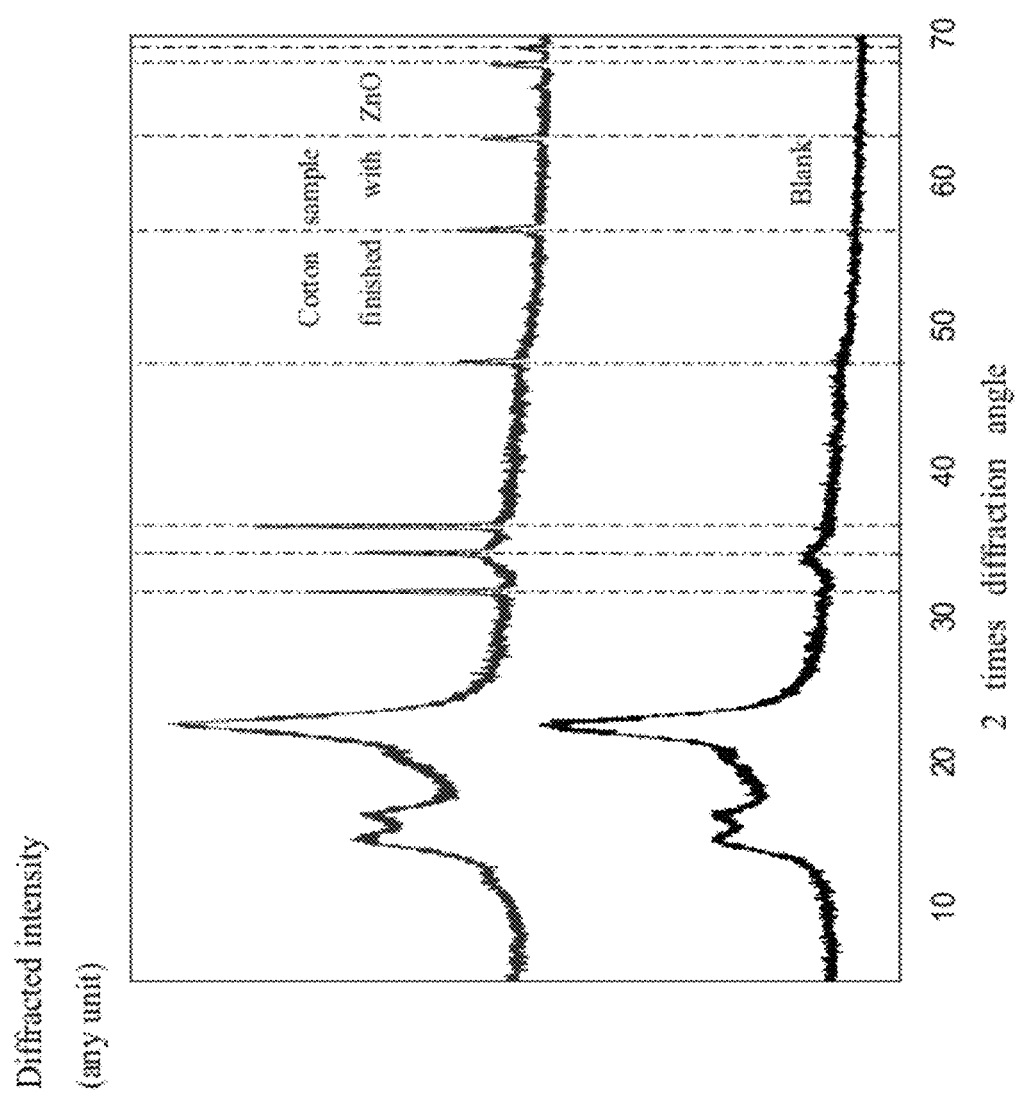
FIG. 6 is an X-ray diffractogram in accordance with one embodiment of the invention.

FIG. 6 shows that the characteristic peak position is that the peak difference between a cotton fabric finished with ZnO and a blank sample is perpendicular to the diffraction angle corresponding to a dotted line. In ordinary circumstances, if the characteristic peak is equal to or greater than 2, the existence of ZnO can be proven. Meanwhile, the characteristic peak position reflects the finished ZnO is rutile type ZnO.

The average grain size of the finishing material can be calculated according to the Scherrer formula:

$$D=0.89\pi\lambda/(B\cos\theta)$$

Wherein D refers to average grain size, nm; 0.89 is a constant; λ refers to the wavelength of X-rays, the Kα X-ray is emitted by using a Cu target, and the average grain size is 0.154 nm; B refers to the diffraction peak width at half-height, and it's required to be converted into radian; θ refers to the diffraction angle corresponding to the peak position. This formula is available in the range of 1-100 nm.

The average grain size of ZnO in FIG. 6 is as follows:

$$D1=0.89\times0.154/[(0.24°\times\pi180°)\times\cos 18.13°]=44\text{ nm}$$

The textile is determined as a nano woven fabric finished with ZnO according to the detection procedure above.

Generally, when the nano power material is finished into the woven fabric by an enterprise, because the process is not stable, the shape of grains is various. ZnO is taken as an example, its shape may be granular, when ZnO contains obvious crystal property, its shape may be flaky, and ZnO is easily confused with a finishing liquor. At the moment, more elemental analysis is required for confirmation.

Example 4

Observing an unknown textile by appearance, and determining the textile which are thin and light, fine in texture and free from grain, has adsorbability and also has a certain ductility during the tearing process, and cannot be split or twisted to obtain single yarns as a non-woven fabric.

Figure 7:
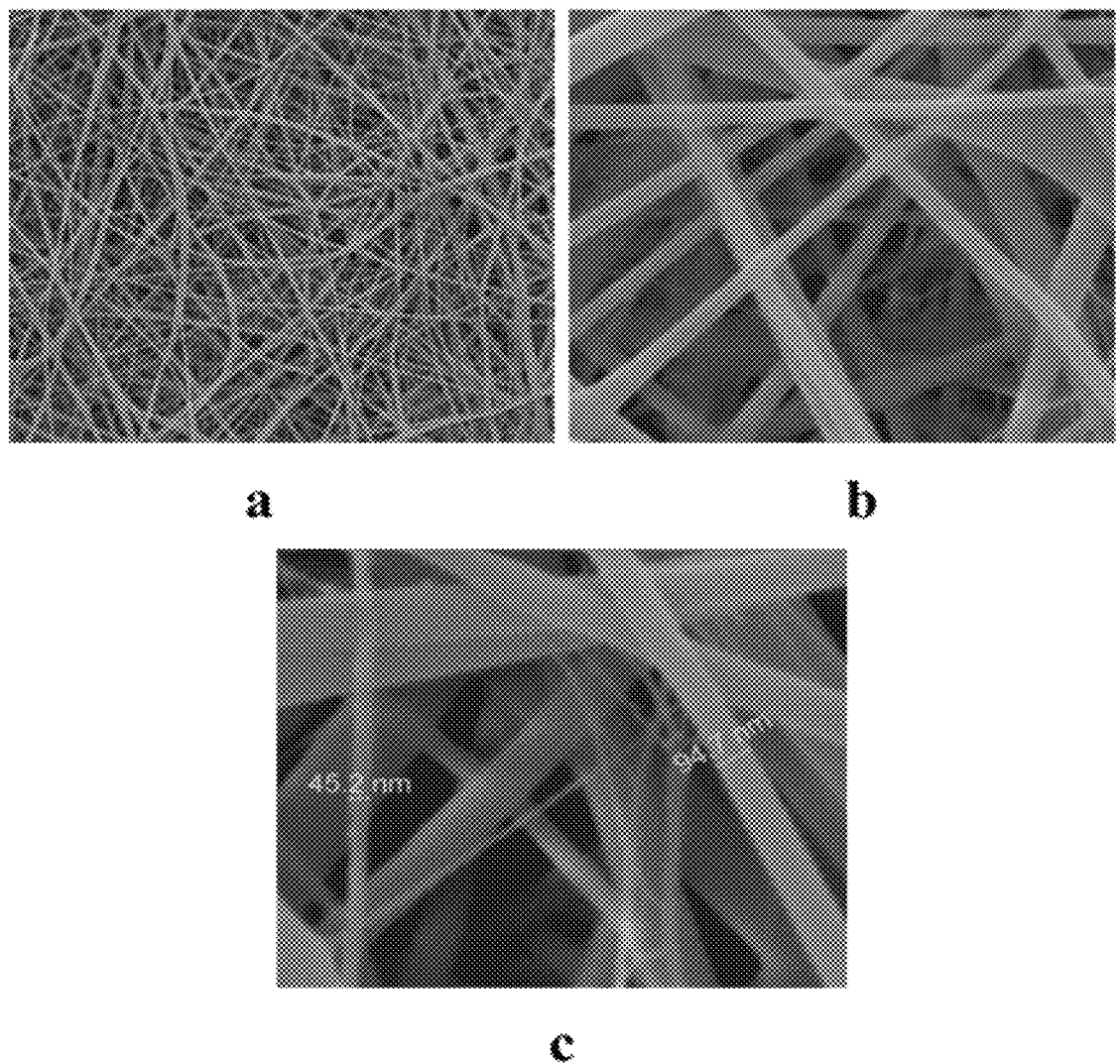
FIG. 7 shows scanning electron microscope photos of a non-woven fabric in accordance with one embodiment of the invention under different multiples; wherein a, b, c, and d represent under 5,000 multiples, under 30,000 multiples, under 30,000 multiples, and under 30,000 multiples, respectively.

Detecting the non-woven fabric by scanning electron microscopy: randomly shearing five 5 mm×5 mm samples on the textile with a pair of clean scissors during the sampling process, and marking the to-be-detected surfaces; holding the samples with a pair of forceps and fixing the samples on a sample support stuck with conductive adhesive tapes, and keeping the to-be-detected surfaces of the samples upward; moving the sample support carried with samples to an ion sputter, and sputtering a metal conductive film on the sample support; transferring the sample support sputtered with the metal conductive film in a scanning electron microscope sample room, and vacuumizing until the scanning electron microscopy test can be carried out. Four areas are randomly selected for observing imaging, see FIG. 7. Under a high-magnification scanning electron microscope, 15 fibers are randomly selected from four areas for measuring its diameter.

Figure 8:
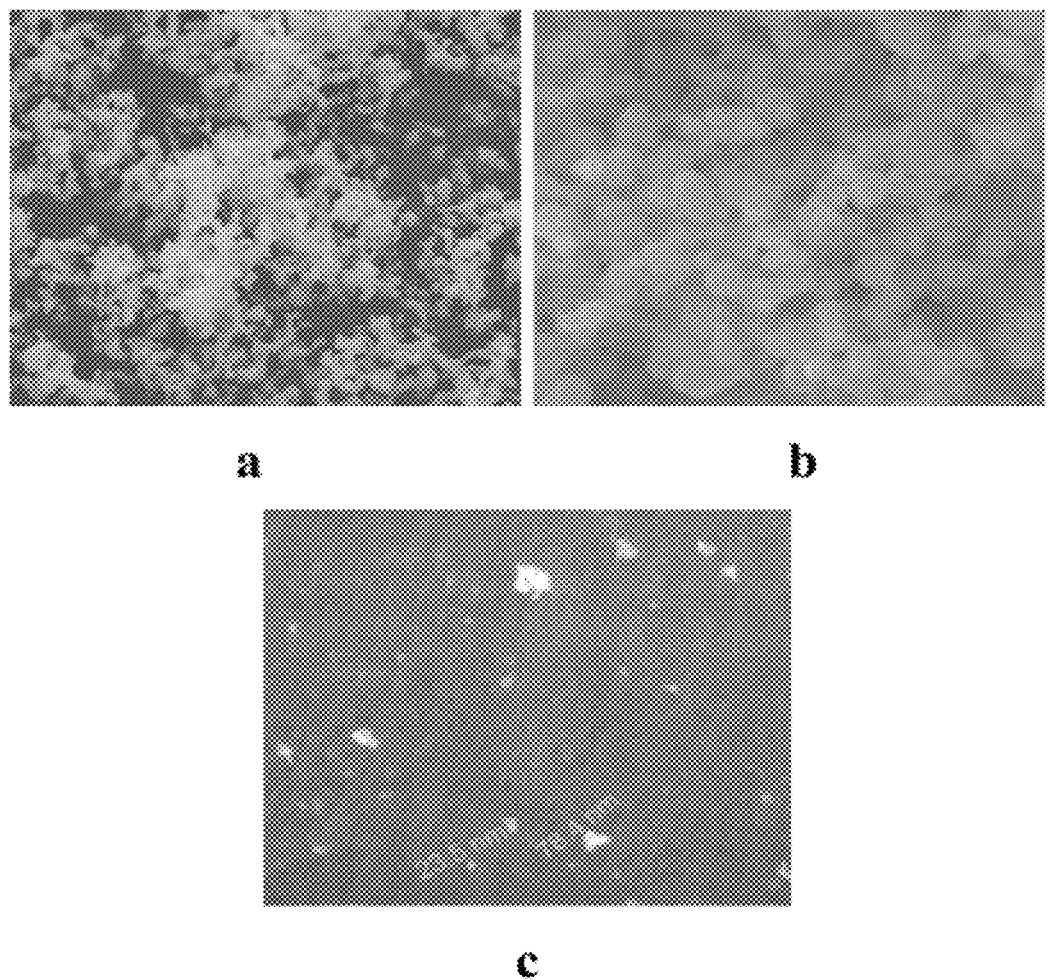
FIG. 8 shows an ash diagram (SEM) of a non-woven fabric in accordance with one embodiment of the invention under different multiples, wherein a, b, and c represent under 5,000 multiples, under 10,000 multiples, and under 20,000 multiples, respectively.
Figure 9:
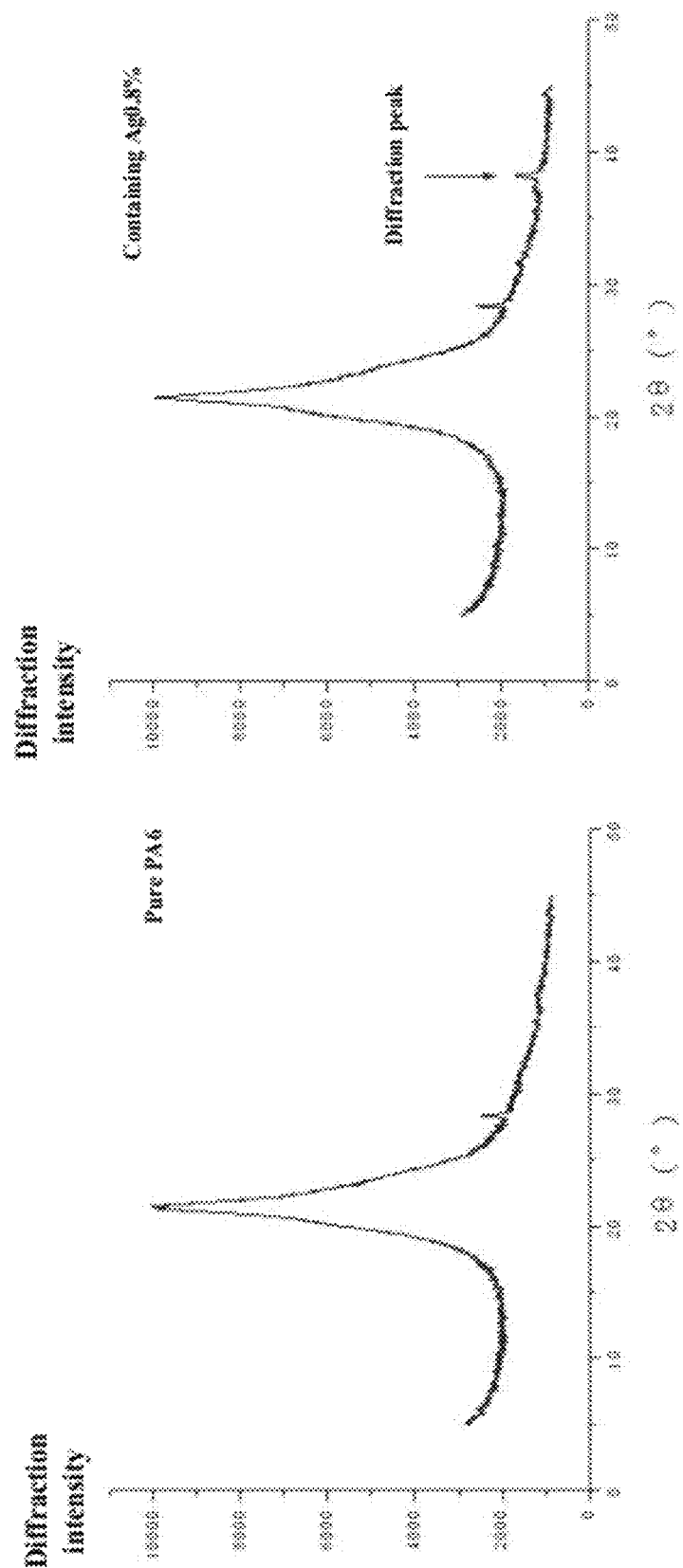
FIG. 9 shows an X-ray diffractogram of a non-woven fabric in accordance with one embodiment of the invention.

The average diameter of the 15 fibers is calculated and smaller than 100 nm. The fiber is more uniform in thickness, and thus the textile can be determined as a nano non-woven fabric. 0.5 g of a sample to be tested is carbonized in a crucible at 500° C. for 4 hours. The resulting ash is analyzed using a scanning electron microscopy and nano grains with a size smaller than 100 nm are detected (as shown in FIG. 8). The sample is determined using an X-ray diffractometer and the grain size of Ag powders in the fibers according to the Scherrer formula is calculated to be 38.61 nm (as shown in FIG. 9).

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for identifying a nano textile, comprising:
   1) determining by appearance whether a textile is a woven fabric or a non-woven fabric, if the textile is a woven fabric, executing step 2); otherwise, executing step 6);
   2) detecting the woven fabric using a scanning electron microscopy, setting a plurality of observation areas or observation points, and performing elemental analysis;
   3) if results of the elemental analysis of step 2) show that grains on the surface of the woven fabric do not comprise Ti, Zn, or Ag, deeming the woven fabric not to be a nano textile; if results of the elemental analysis of step 2) show that grains on the surface of the woven fabric comprise Ti, Zn, or Ag, executing step 4);
   4) determining a crystal form and an average grain size of a finishing material in the grains by using an X-ray diffractometer;
   5) if the average grain size of the finishing material is smaller than 100 nm, deeming the woven fabric to be a nano textile; if the average grain size of the finishing material is equal to or greater than 100 nm, deeming the textile not to be a nano textile;
   6) detecting the non-woven fabric and measuring the diameter of fibers of the non-woven fabric using scanning electron microscopy;
   7) if the diameter of the fibers is smaller than 100 nm, deeming the non-woven fabric to be a nano textile, then establishing observation points of the fibers, and performing elemental analysis; if the diameter of the fibers is not smaller than 100 nm, deeming the non-woven fabric not to be a nano textile; and
   8) if results of the elemental analysis of step 7) show that the fibers contain Ti, Zn, or Ag, deeming the non-woven fabric to be a nano textile fused with a finishing material; otherwise, deeming the non-woven fabric to be a nano textile not fused with a finishing material.

2. The method of claim 1, wherein step 4) comprises:
   a) scanning the textile on an X-ray diffractometer;
   b) taking a two times diffraction angle as a horizontal coordinate and a diffracted intensity as a vertical coordinate;
   c) determining the crystal form of the finishing material in the grains on the textile according to the relationship between the characteristic peak position and intensity; and
   d) calculating the average grain size of the finishing material in the grains according to a Scherrer formula.

3. The method of claim 1, wherein the step of detecting the woven fabric using the scanning electron microscopy comprises:
   a) sputtering a metal conductive film on the textile surface with an ion sputter; and
   b) feeding samples into a scanning electron microscope for scanning electron microscopy imaging.

4. The method of claim 1, wherein the step of detecting the non-woven fabric using the scanning electron microscopy comprises:
   c) sputtering a metal conductive film on the textile surface with an ion sputter; and
   d) feeding samples into a scanning electron microscope for scanning electron microscopy imaging.

5. The method of claim 1, wherein in step 1), the step of determining by appearance comprises determining whether the textile is a woven fabric or non-woven fabric according to the texture of the textile, whether the textile has obvious horizontal and longitudinal grains, and whether the textile can be split or twisted to obtain single yarns.

* * * * *